US012565461B2

(12) United States Patent
Grossmann

(10) Patent No.: US 12,565,461 B2
(45) Date of Patent: Mar. 3, 2026

(54) PROCESS FOR PREPARING BROMOCHLOROMETHANE

(71) Applicant: SALTIGO GmbH, Leverkusen (DE)

(72) Inventor: Andre Grossmann, Cologne (DE)

(73) Assignee: Saltigo GmbH, Leverkusen (DE)

( * ) Notice: Subject to any disclaimer, the term of this patent is extended or adjusted under 35 U.S.C. 154(b) by 589 days.

(21) Appl. No.: 17/780,568

(22) PCT Filed: Nov. 27, 2020

(86) PCT No.: PCT/EP2020/083710
§ 371 (c)(1),
(2) Date: May 27, 2022

(87) PCT Pub. No.: WO2021/105412
PCT Pub. Date: Jun. 3, 2021

(65) Prior Publication Data
US 2022/0411353 A1     Dec. 29, 2022

(30) Foreign Application Priority Data
Nov. 28, 2019    (EP) ...................................... 19212198

(51) Int. Cl.
*C07C 17/20*        (2006.01)
*C07C 17/383*       (2006.01)
(52) U.S. Cl.
CPC .......... *C07C 17/202* (2013.01); *C07C 17/383* (2013.01)
(58) Field of Classification Search
CPC .............................. C07C 17/20; C07C 17/202
See application file for complete search history.

(56) References Cited

U.S. PATENT DOCUMENTS 2,694,094 A     11/1954  Lobos

FOREIGN PATENT DOCUMENTS

| CN | 101357877 A | 2/2009 |
|---|---|---|
| CN | 101913981 A | 12/2010 |
| DE | 2133152 A1 | 1/1973 |
| GB | 995960 A | 6/1965 |
| GB | 2226311 A | 6/1990 |
| SU | 1587036 A1 | 8/1990 |

OTHER PUBLICATIONS

Machine translation of patent No. SU1587036A1; Aug. 23, 1990; pp. 1-5 (Year: 1990).*
European Search Report from corresponding European Application No. 19212198, dated May 4, 2020, three pages.
Forbes, George S. "Rearrangements in Compounds of Carbon, Silicon, Germanium and Tin containing Halogens, Isocyanate and Thiocyanate", Journal of the American Chemical Society, Bd. 67, Nr. 11, 1. (Jan. 1, 1945), XP055686758, pp. 1911-1914.
Patent Office of the Government of India Hearing adjournment notice In reference of Application No. 202237029107 dated Oct. 28, 2025, three pages.

* cited by examiner

*Primary Examiner* — Medhanit W Bahta
(74) *Attorney, Agent, or Firm* — Nicanor A. Kohncke; Christopher L. McDavid; Alyson J. DiLena

(57)            ABSTRACT

The invention relates to an improved process for preparing bromochloromethane by reacting dichloromethane and dibromomethane in the presence of catalysts.

8 Claims, No Drawings

PROCESS FOR PREPARING
BROMOCHLOROMETHANE

The invention relates to an improved process for preparing bromochloromethane by reacting dichloromethane and dibromomethane in the presence of catalysts.

Bromochloromethane is an important solvent in chemical processes and is also advantageously used in chemical reactions, for example in cyclopropanation reactions such as the Simmons-Smith reaction, as a reagent for preparing an intermediate zinc carbene (carbenoid).

Processes for preparing bromochloromethane are known. For example, DE2133152 A1 discloses the preparation of fluorine-free haloalkanes such as dichloromethane or bromochloromethane from fluorine-containing haloalkanes such as dibromodifluoromethane in the presence of aluminum trichloride or aluminum tribromide. In this way, for example, bromochloromethane is obtained in yields of 19% of theory. The disadvantage of this method is that the starting materials are very expensive and waste streams containing fluorine are formed during the reaction. SU1587036 discloses a process for preparing mixed polyhaloalkanes such as bromochloromethane or chloroiodomethane by reacting dichloromethane and dibromomethane in the presence of aluminum trichloride. In this case, a mixture of the three substances dichloromethane, dibromomethane and bromochloromethane is formed in an equilibrium reaction, with bromochloromethane, for example, being obtained in yields of 76% of theory. A disadvantage of this process is that the process requires discontinuous extractive aqueous work-up and subsequent discontinuous fractional distillation and the yields are not sufficient for an economical industrial process. In addition, the yield of bromochloromethane based on the bromine atoms used is insufficient. There was therefore still the object of improving the process according to the prior art in such a way that the disadvantages are avoided and at the same time the yield is significantly increased.

Surprisingly, a process for preparing bromochloromethane has been found in which at least a) dibromomethane and dichloromethane is reacted with at least one catalyst selected from the group comprising aluminum trichloride, aluminum tribromide, iron(II) chloride, iron(III) chloride, nickel chloride, zinc chloride, boron trifluoride, tetraalkylphosphonium halide, tetraalkylphosphonium tosylate, tetraalkylphosphonium mesylate, tetraalkylphosphonium triflate, tetraarylphosphonium halide, tetraarylphosphonium tosylate, tetraarylphosphonium mesylate or tetraarylphosphonium triflate, whereby a first crude mixture comprising at least dibromomethane, dichloromethane and bromochloromethane is obtained, and b i) at least one alcohol is added to the first crude mixture obtained in step a), resulting in the formation of a monophasic second crude mixture, which comprises an organic phase comprising dibromomethane, dichloromethane and bromochloromethane, or b ii) water and optionally at least one alcohol is added to the first crude mixture obtained in step a), resulting in the formation of a biphasic second crude mixture, which comprises an organic phase comprising at least dibromomethane, dichloromethane and bromochloromethane, and an aqueous phase, and the organic phase is separated off from the aqueous phase.

c) the components dibromomethane, dichloromethane and bromochloromethane are separated from one another, preferably by distillation, from the monophasic second crude mixture from step b i), or from the separated organic phase from step b ii).

Steps a), b i) and b ii) of the process according to the invention are preferably carried out discontinuously. According to the invention, discontinuous implementation means that the reaction takes place with interruptions, for example in several successive reactions, in the same reactor or in different reactors. In the case of discontinuous implementation, it is possible for there to be periods both of continuous separation alongside periods of discontinuous separation.

In step a) of the process according to the invention, preference is given to using dichloromethane and dibromomethane at a molar ratio of from 1:10 to 10:1, preferably from 1:1 to 10:1, particularly preferably from 1:1 to 3:1. Typically, dichloromethane and dibromomethane are initially charged, preferably in a first reactor, and mixed, preferably hydraulically or mechanically. The dichloromethane and dibromomethane used preferably have a water content of less than 2000 mg per kg of dihalomethane.

To this mixture is then added a catalyst selected from the group comprising aluminum trichloride, aluminum tribromide, iron(II) chloride, iron(III) chloride, nickel chloride, zinc chloride, boron trifluoride, tetraalkylphosphonium halide, tetraalkylphosphonium tosylate, tetraalkylphosphonium mesylate, tetraalkylphosphonium triflate, tetraarylphosphonium halide, tetraarylphosphonium tosylate, tetraarylphosphonium mesylate or tetraarylphosphonium triflate. The catalysts, preferably the catalysts which can react with water, are present in anhydrous form. Anhydrous aluminum trichloride and anhydrous aluminum tribromide are preferred as catalysts. In a preferred embodiment, the reaction mixture is mixed, preferably hydraulically or mechanically. In step a), the molar ratio of catalyst to dichloromethane is preferably from 0.001 to 0.2, preferably from 0.05 to 0.15, if dichloromethane and dibromomethane are used at a molar ratio of 1:1 or greater. The molar ratio of catalyst to dibromomethane in step a) is likewise preferably from 0.001 to 0.2, preferably from 0.05 to 0.15, if dichloromethane and dibromomethane are used at a molar ratio of less than 1:1.

The reaction of dichloromethane and dibromomethane in step a) of the process according to the invention is preferably carried out at temperatures of from 40 to 150° C., preferably from 50 to 100° C., particularly preferably from 50 to 60° C.

This usually results in a product mixture comprising 2 to 70% by weight dichloromethane, 6 to 73% by weight dibromomethane, 24 to 50% by weight bromochloromethane, preferably 24 to 45% by weight bromochloromethane, and up to 2% by weight of other components, the contents of dichloromethane, dibromomethane, bromochloromethane and any other components adding up to 100% by weight. The course of the reaction can be monitored regularly by means of in-process control, for example by gas chromatography. When the reaction has reached the desired level, the first crude mixture is usually worked up by bringing it into contact with water and/or alcohol.

For this purpose, the first crude mixture is usually brought into contact with at least water and/or at least one alcohol in step b i) or step b ii) of the process according to the invention. As a result, reactive intermediates formed in the reaction in step a), and/or the catalyst, for example aluminum trichloride, are hydrolyzed and/or reacted via alcoholysis. The bringing into contact can be effected, for example, by mixing, the mixing preferably taking place mechanically, particularly preferably using a stirrer, and/or hydraulically, particularly preferably by pumping.

The bringing into contact of at least water and/or at least one alcohol with the mixture from step a) can be carried out continuously or discontinuously. In step b i), at least one alcohol is preferably initially charged in a reactor, particularly preferably in a second reactor, and then the first crude mixture from step a) is added, usually with mechanical and/or hydraulic mixing.

This results in a monophasic second crude mixture comprising an organic phase containing dibromomethane, dichloromethane and bromochloromethane. Suitable alcohols for step b i) are typically methanol, ethanol or isopropanol.

In step b ii), water and optionally at least one alcohol is preferably initially charged in a reactor, particularly preferably in a second reactor, and then the first crude mixture from step a) is added, usually with mechanical and/or hydraulic mixing.

This results in a biphasic second crude mixture comprising an organic phase containing dibromomethane, dichloromethane and bromochloromethane, and also an aqueous phase.

After the first crude mixture from step a) has been brought into contact with at least one alcohol according to step b i) or with water according to step b ii), the second crude mixture can be mixed hydraulically and/or mechanically for a period of 15 to 300 minutes in order to complete the hydrolysis or alcoholysis of intermediates formed during the reaction.

If, after bringing at least one alcohol into contact with the reaction mixture from step a) in step b i), a monophasic second crude mixture is present, the mixture can be separated directly by distillation.

If, after bringing water, and optionally at least one alcohol, into contact with the first crude mixture from step a) in step b ii), a biphasic second crude mixture is present, the aqueous phase is then separated off from the organic phase according to step b ii) of the process according to the invention.

In step c) of the process according to the invention, the components dibromomethane, dichloromethane and bromochloromethane are preferably separated from one another from the monophasic second crude mixture from step b i) and/or from the separated organic phase of the second crude mixture from step b ii).

Step c) of the process according to the invention can preferably be carried out in such a way that c i) firstly dichloromethane is separated off from the monophasic second crude mixture from step b i) or from the separated organic phase of the second crude mixture from step b ii), and c ii) subsequently dibromomethane and bromochloromethane are isolated as separate fractions.

The components dibromomethane, dichloromethane and bromochloromethane are separated from the monophasic second crude mixture from step b i) and/or from the separated organic phase of the second crude mixture from step b ii) in accordance with step c, c i) and/or c ii), preferably by distillation, and the separation is particularly preferably carried out continuously.

According to the invention, continuous separation is defined in such a way that it takes place without interruption, for example in one or more distillation columns. According to the invention, discontinuous separation means that the separation, for example in a plurality of discrete distillation steps with the same or with different distillation columns, takes place with interruptions. In the case of discontinuous separation, it is possible for there to be periods both of continuous separation alongside periods of discontinuous separation.

In this case, preferably in step c i), particularly preferably in a first distillation column, dichloromethane may be obtained as distillate and the mixture of dibromomethane and bromochloromethane as bottom product.

In step c ii), the mixture of dibromomethane and chlorobromomethane can preferably be fed, particularly preferably into a second distillation column, and bromochloromethane can then be obtained as distillate and dibromomethane as bottom product.

In a particularly preferred embodiment of the process according to the invention, steps c i) and c ii) are carried out in two different distillation columns which are connected to each other in a communicating manner in such a way that the bottom product from the distillation column in which step c i) is carried out is continuously fed to a second distillation column, preferably into the side stream of a second distillation column. In parallel, in this preferred embodiment, bromochloromethane is removed continuously from the second distillation column as distillate and dibromomethane is removed continuously as bottom product.

In step c i) of the process according to the invention, a mixture is obtained, preferably as distillate, which comprises dichloromethane at a content of 95 to 99.9% by weight, based on the total mass of the distillate, and any other components at a content of 0.1 to 5% by weight, based on the total mass of the distillate.

In step c i) of the process according to the invention, a mixture is obtained, preferably as bottom product, which comprises dibromomethane at a content of 25 to 40% by weight, based on the total mass of the bottoms, and bromochloromethane at a content of 60 to 75% by weight, based on the total mass of the bottoms.

In step c ii) of the process according to the invention, a mixture is obtained, preferably as distillate, which comprises bromochloromethane at a content of 95 to 99.9% by weight, based on the total mass of the distillate. In step c ii) of the process according to the invention, a mixture is obtained, preferably as bottom product, which comprises dibromomethane at a content of 95 to 99.9% by weight, based on the total mass of the bottoms.

The dichloromethane obtained from step c i) and/or the dibromomethane obtained from step c ii) may preferably be reused in step a) of a subsequent preparation of bromochloromethane.

The total yield of bromochloromethane, based on "freshly used" bromine component, meaning "not recovered from a previous process according to the invention", in a process according to the invention carried out continuously, is between 90 and 99 percent of theory, preferably between 93 and 97 percent of theory. Here, twice the molar amount of dibromomethane used in step a) is calculated as the bromine component, since two moles of bromochloromethane are theoretically formed from one mole of dibromomethane.

In a further preferred embodiment, the process according to the invention may be carried out in such a way that the reaction of dibromomethane and dichloromethane with at least one catalyst is carried out continuously, in accordance with step a), by reacting a first amount of dichloromethane and a first amount of dibromomethane in the presence of a first amount of catalyst, with further amounts of dibromomethane, dichloromethane and catalyst then being added continuously to the reaction mixture in the same ratio, at the same time a portion of the components dibromomethane, dichloromethane and bromochloromethane is separated off from the reaction mixture, preferably by distillation, in accordance with step c), and subsequently dichloromethane is separated off continuously from the reaction mixture in accordance with step c i), and then dibromomethane and bromochloromethane are isolated continuously as separate fractions in accordance with step c ii). In this embodiment of the process according to the invention, which is carried out fully continuously, steps b i) and/or b ii), i.e. the hydrolysis and/or alcoholysis of the catalyst, are omitted.

With the process according to the invention, it is now possible to produce bromochloromethane in high yields and high purities in a simple and energy-efficient manner without harmful waste streams.

EXAMPLES

Example 1 (Inventive)

7329 g (84.9 mol) of dichloromethane and 7500 g (43.15 mol) of dibromomethane, each having a water content of less than 2000 mg/kg, were mixed at 25° C. in a first reactor and 73.9 g (0.55 mol) of anhydrous aluminum trichloride at 25° C. were added. The temperature of the reaction mixture is then increased to 52 to 55° C. and the boiling mixture is stirred for a further 2 hours. The course of the reaction is regularly monitored by means of an in-process control by gas chromatography. When the content of bromochloromethane in the reaction mixture was in the range of 45 to 46 area percent, the reaction was terminated by transferring the reaction mixture to a second reactor, in which 3750 g of water had been initially charged, with stirring of the resulting mixture for 1 hour at 20 to 25° C. After completion of the addition of the reaction mixture from the first reactor, the resulting biphasic second reaction mixture was stirred at 20 to 25° C. for a further hour. Subsequently, the organic phase, usually the lower phase, and then the aqueous phase were removed from the second reactor and the lower organic phase was introduced via an evaporator into a continuous distillation apparatus in the mid-section as vapor at a temperature of 91° C. at a pressure of 3 bar. 4604 g of a low-boiling fraction containing 99% by weight dichloromethane were removed as distillate at the top of the first distillation column at a top temperature of 65° C. at 3 bar pressure. At the same time, a bottom product was removed from the first distillation column, which predominantly contained a mixture of dibromomethane and bromochloromethane. This bottom product was introduced as a side stream into a second distillation column. 6901 g (52.91 mol) of a low-boiling fraction containing 99% by weight bromochloromethane was removed as distillate at the top of the second distillation column at a top temperature of 58° C. at 1 bar pressure. This corresponds to a yield of 61.3 percent of theory. The top stream from the first distillation column containing 99% by weight dichloromethane, and the bottoms (6901 g) from the second distillation column containing 99% by weight dibromomethane, were used in a further preparation of bromochloromethane. After 10 cycles of the reaction, the yield of bromochloromethane is 95% of theory, based on the bromine component used.

Example 2 (Inventive)

513 g (6.01 mol) of dichloromethane and 300 g (1.73 mol) of dibromomethane, each having a water content of less than 2000 mg/kg, were mixed at 25° C. in a first reactor and 5.75 g (42.7 mmol) of anhydrous aluminum trichloride at 25° C. were added. The temperature of the reaction mixture was then increased to 46 to 49° C. and the boiling mixture was stirred for a further 2 hours. The course of the reaction is regularly monitored by means of an in-process control by gas chromatography. When the content of bromochloromethane in the reaction mixture did not increase any further, the reaction was terminated by cooling the reaction mixture to 25 to 30° C. and then deactivating the catalyst by adding 5.06 g (0.13 mol) of ethanol with stirring. The composition of the vaporizable portion of the reaction mixture was determined by gas chromatography to be 47% by weight dichloromethane, 11% by weight dibromomethane and 42% by weight bromochloromethane.

Analogously to Example 1, the reaction mixture can then be separated directly by means of distillation into the components dichloromethane, dibromomethane and bromochloromethane in purities of at least 95 percent by weight.

What is claimed is:

1. A process for preparing chlorobromomethane, comprising a) reacting dibromomethane and dichloromethane with at least one catalyst selected from the group consisting of aluminum trichloride, aluminum tribromide, iron (II) chloride, iron (III) chloride, nickel chloride, zinc chloride, boron trifluoride, tetraalkylphosphonium halide, tetraalkylphosphonium tosylate, tetraalkylphosphonium mesylate, tetraalkylphosphonium triflate, tetraarylphosphonium halide, tetraarylphosphonium tosylate, tetraarylphosphonium mesylate and tetraarylphosphonium triflate, whereby a first crude mixture comprising at least dibromomethane, dichloromethane and bromochloromethane is obtained, and b i) adding at least one alcohol to the first crude mixture obtained in step a), resulting in the formation of a monophasic second crude mixture, which comprises an organic phase comprising at least alcohol, dibromomethane, dichloromethane and bromochloromethane, or b ii) adding water and optionally at least one alcohol to the first crude mixture obtained in step a), resulting in the formation of a biphasic second crude mixture, which comprises an organic phase comprising at least dibromomethane, dichloromethane and bromochloromethane, and an aqueous phase, and the organic phase is separated off from the aqueous phase, c) separating the components dibromomethane, dichloromethane and bromochloromethane from one another from the monophasic second crude mixture from step b i), or from the separated organic phase of the second crude mixture from step b ii) by c i) firstly separating off dichloromethane as a first distillate over a first distillation column, said first distillate comprising dichloromethane at a content of 95 to 99.9% by weight based on the total mass of the distillate, from the monophasic second crude mixture from step b i) and/or from the separated organic phase of the second crude mixture from step b ii), and c ii) subsequently feeding a bottom portion from the distillation of step c i) into a second distillation column, the bottom portion comprising dibromomethane at a content of from 25 to 40% by weight based on total mass of the bottom portion and bromochloromethand at a content of 60 to 76% by weight based on total mass of the bottom portion, isolating bromochloromethane as a second distillate with a content of from 95 to 99.9% by weight based on the total mass of the second distillate and isolating dibromomethane as a bottom portion of from the distillation step c ii) in a content of 95 to 99.5% by weight based on the total weight of the bottom portion from distillation step c ii), and d) using the dichloromethane obtained from step c i) and the dibromomethane obtained from step c ii) in step a) of a subsequent preparation of bromochloromethane that comprises said steps a) to c).

2. The process as claimed in claim 1, wherein in step a) the dichloromethane and the dibromomethane are used at a molar ratio of from 1:10 to 10:1.

3. The process as claimed in claim 1, wherein in step a) a molar ratio of the catalyst to the dichloromethane is from 0.001 to 0.2, if the dichloromethane and the dibromomethane are used at a molar ratio of 1:1 or greater.

4. The process as claimed in claim 1, wherein in step a) a molar ratio of the catalyst to the dibromomethane is from 0.001 to 0.2, if the dichloromethane and the dibromomethane are used at a molar ratio of less than 1:1.

5. The process as claimed in claim 1, wherein step a) is carried out at temperatures of 40 to 150° C.

6. The process as claimed in claim 1, wherein step a) and/or step b i) and/or step b ii) are carried out discontinuously.

7. The process as claimed in claim 1, wherein in step c), step c i) and/or step c ii), the dibromomethane, the dichloromethane and the bromochloromethane present in the monophasic second crude mixture from step b i) and/or in the separated organic phase of the second crude mixture from step b ii) are separated from one another by distillation.

8. The process as claimed in claim 1, wherein the steps c), c i) and/or c ii) are carried out continuously.

* * * * *